United States Patent [19]

Nelson et al.

[11] Patent Number: 4,676,883
[45] Date of Patent: Jun. 30, 1987

[54] OPTICAL DISK TRANSMISSION MONITOR FOR DEPOSITED FILMS

[75] Inventors: Roger E. Nelson; Clyde L. Lucky, both of Sylmar, Calif.

[73] Assignee: Sierracin Corporation, Sylmar, Calif.

[21] Appl. No.: 835,157

[22] Filed: Mar. 3, 1986

[51] Int. Cl.⁴ .............................................. C23C 14/00
[52] U.S. Cl. ...................................... 204/298; 118/712; 118/715; 204/192.13; 356/382; 356/435
[58] Field of Search .............. 204/298, 192 R, 192.13; 118/715, 712; 356/382, 435

[56] References Cited

U.S. PATENT DOCUMENTS

| | | | |
|---|---|---|---|
| 3,744,916 | 7/1973 | Bey et al. | 118/712 |
| 3,853,093 | 12/1974 | Baker et al. | 118/715 |
| 4,024,291 | 5/1977 | Wilmanns | 204/298 |
| 4,207,835 | 6/1980 | Schwieker | 118/712 |
| 4,569,717 | 2/1986 | Ohgami | 356/382 |
| 4,582,431 | 4/1986 | Cole | 356/382 |

FOREIGN PATENT DOCUMENTS

| 2029017 | 3/1980 | United Kingdom | 356/382 |
|---|---|---|---|
| 315019 | 7/1971 | U.S.S.R. | 356/382 |

Primary Examiner—Arthur P. Demers
Attorney, Agent, or Firm—Saul Epstein

[57] ABSTRACT

An optical transmission monitor for determining the optical transmissivity and thickness of films deposited on a substrate. A monitor substrate in the form of a rotating disk exposed to the deposition process is used. An optical system for measuring the transmissivity of the disk obstructs a fixed segment of the rotating disk so that the film thickness on the monitor disk is a known fraction of the film on the substrate being processed.

12 Claims, 6 Drawing Figures

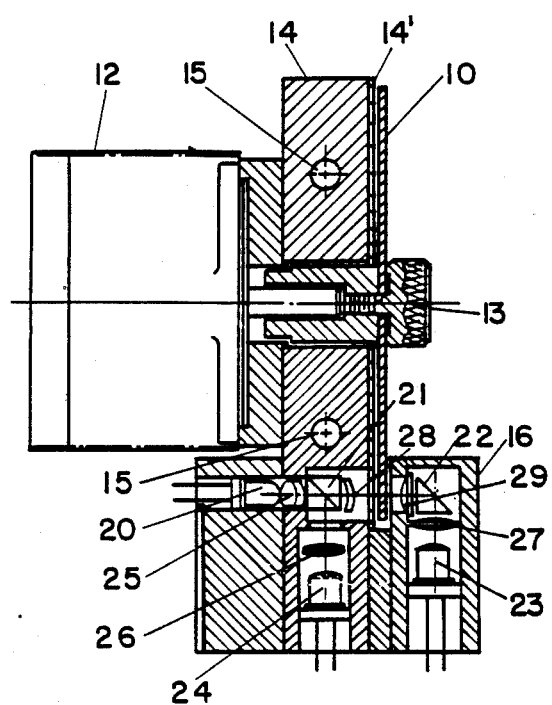
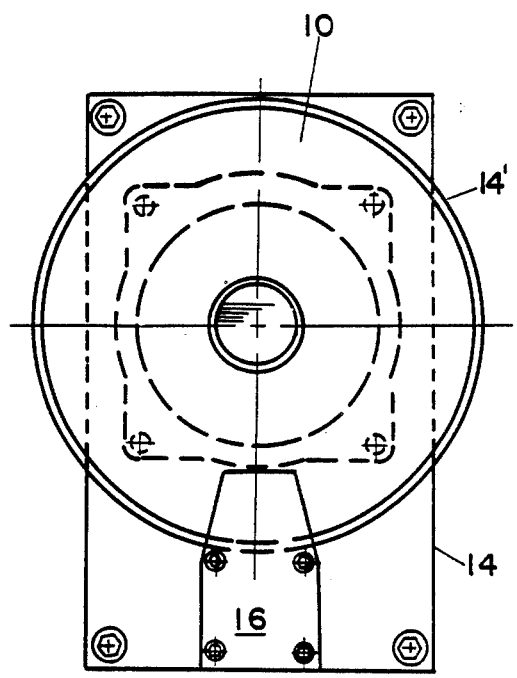
FIG 1                FIG 2
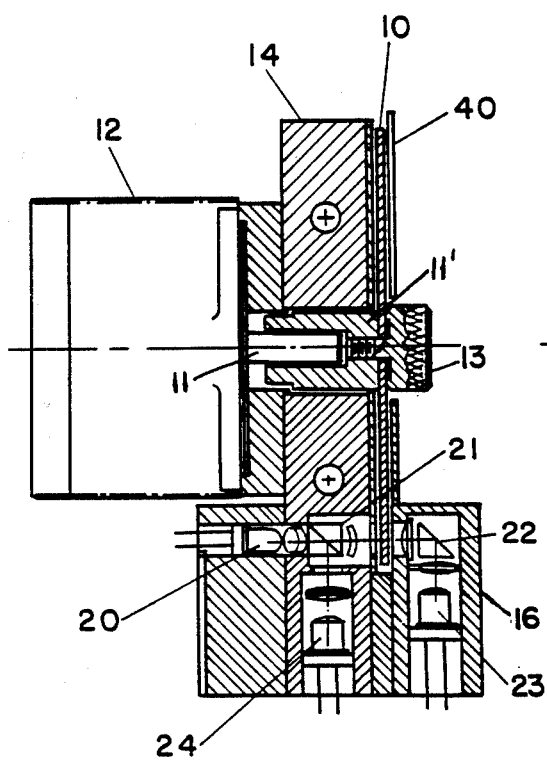
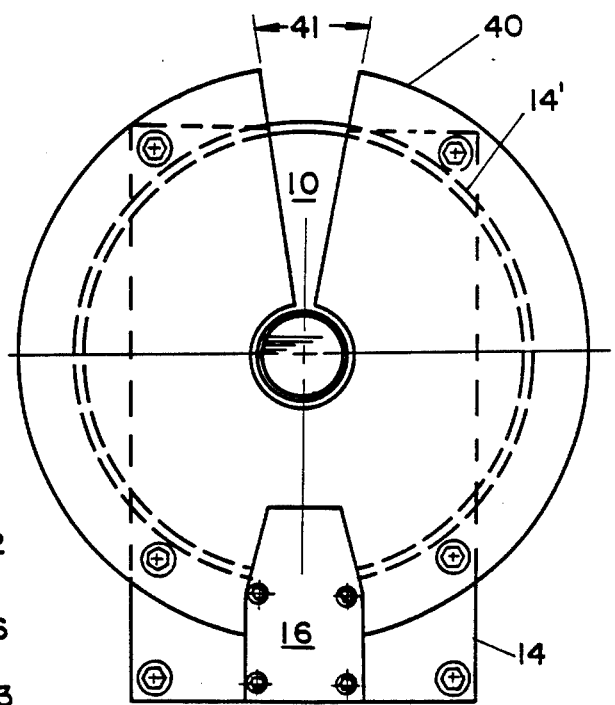
FIG 4                FIG 5

OPTICAL DISK TRANSMISSION MONITOR FOR DEPOSITED FILMS

BACKGROUND OF THE INVENTION

This invention relates to the measurement of the optical characteristics of deposited thin films. More specifically, the present invention provides a continuous measurement of the optical transmissivity of a film as it is being deposited on a substrate. Such a measurement is useful in a variety of situations.

As an example, bubble canopies and windshields of aircraft are often coated with an electrically conductive transparent film which allows the canopy or windshield to be heated, and it is desirable to continuously measure the optical transmission through the windshield during the coating process so as to ensure adequate clarity of the coating. Also, since the optical transmission through a deposited thin film is a function of its thickness, the present invention can be used as an indirect measurement of film thickness. For films having an optical thickness much less than one-quarter wavelength of the light passing through it, the optical transmission is inversely related to its thickness. For thicker films, the thickness also affects transmission due to the interference pheonomenon caused by the internal reflections present in the film.

One common way of depositing a thin film on a substrate is known as "sputtering". This process is carried out in a partial vacuum under the influence of an electric field. A continuous measurement of optical transmission through the part being coated is difficult because of the problems involved in appropriately locating the optical measurement components to avoid shadowing.

Even those prior art instruments which entail the use of auxiliary substrates to monitor the process include optical systems which have disadvantages. See for example, U.S. Pat. Nos. 2,771,055 and 3,063,867.

The sputtering process mentioned above involves the use of a cathode fitted with or comprised of the target material to be sputtered. The cathode is kept at a high negative potential of several kilovolts—up to 5 kV—for diode and triode process configurations, or, at several hundreds of Volts—commonly 300 to 600 Volts—for magnetically enhanced cathode types. This latter type of cathode is commonly used in planarmagnetron and post-magnetron configurations. Radio frequency excitation of the sputtering cathode is also common.

The chamber atmosphere is commonly argon for simple non-reactive sputtering of materials directly onto a substrate. However, a mixture of gases may be used when reactive sputtering is employed. In this latter case, a chemical compound created by a reaction of the target material with the sputter gases is deposited onto the substrate. The pressure of the sputter gases in the vacuum chamber are commonly held at 10 to 100 micron for the non-magnetically enhanced sputtering methods and at 1 to 10 micron for magnetically enhanced methods.

Whatever method is used, the electric field causes ionization of the sputter gases creating a glow discharge. This glow discharge is commonly called the plasma. It exists in the form of a highly energetic cloud of electrons and positively charged sputter gas ions. The ions are attracted to the target and bombard the target surface, ejecting atoms of the target material. These atoms leave the target at high velocity in a distribution pattern determined by the sputtering method and cathode used, and in some cases, the geometry of the cathode and the surrounding apparatus. The substrate to be coated is placed so that these atoms strike the substrate surface and adhere; thus forming a film of the target material (or a compound of the target material if reactive sputter gases are used).

An optical measurement system set up to monitor or control the sputtering process must avoid having parts in a position too near to the object being coated and/or the plasma zone such that it would distort the distribution pattern of the atoms arriving at the object; and thereby "shadowing" the object. This shadowing can cause a nonuniform coating or distort an otherwise intended non-uniform global coating pattern.

Even if an optical system can be set up which avoids shadows, a different optical system must be devised for each application, which of course is inconvenient and expensive. Accordingly, the herein disclosed monitor avoids the difficulties arising because of the placement of the optical components in an optical transmission measuring system for deposited coatings by providing a self contained measuring system which measures the optical transmissivity of a monitor substrate wherein the shadowing effect is controlled.

SUMMARY OF THE INVENTION

The present invention is disclosed in connection with deposition by sputtering, but it will be realized that the invention can be used to monitor deposition by other processes, as for example, high vacuum deposition using E-Beam evaporation sources.

The invented system includes an auxiliary substrate in the form of a rotating disk which is exposed to the sputtering cathode, and is preferably spaced at approximately the same distance from the cathode as is the actual substrate being coated. In a first embodiment, the optical system used to view the monitoring disk obstructs a very small portion of the disk circumference so that the amount of and quality of the sputtered material deposited on the monitoring disk, and consequently its optical transmission, will very nearly be the same as the part being coated. To the extent that the obstruction causes a reduction in the thickness of the coating on the monitor disk, the reduction is a constant proportion, and an appropriate correction can be made in the calibration of the associated electronics or in the interpretation of the resulting data. If the monitor is spaced from the cathode at a distance different than that of the actual substrate, compensation for the difference in deposition rate can be handled in a similar manner.

The optical transmissivity of a coating on a substrate is, of course, related to its thickness, being a function of the thickness related losses of the coating and the thickness related interference effect. Thus the invented monitor provides a measure of coating thickness simultaneously with a measure of the quality (clarity) of the coating.

In some cases the desired thickness of the deposited film is such that it has very low transmissivity, or is in fact opaque. Measurement of the transmissivity may accordingly be difficult or impossible. In such cases, in accordance with a second disclosed embodiment of the invention, the thickness of the coating received by the disk can be made to be some predetermined fraction of the coating received by the substrate. This is accomplished by providing a mask for the rotating disk which covers a significant fraction of the disk surface. If an appropriate fraction is selected, the optical transmissivity of the disk will be in a range which can be conveniently measured so as to provide a measure of the thickness of the film deposited on the actual part being processed.

BRIEF DESCRIPTION OF THE DRAWINGS

FIG. 1 is a partially sectioned side view of a first embodiment of the present invention.

FIG. 2 is a front view of the embodiment shown in FIG. 1.

FIG. 4 is a partially sectioned side view of a second embodiment of the invention.

FIG. 5 is a front view of the embodiment of FIG. 4.

DETAILED DESCRIPTION OF THE INVENTION

Figure 6:
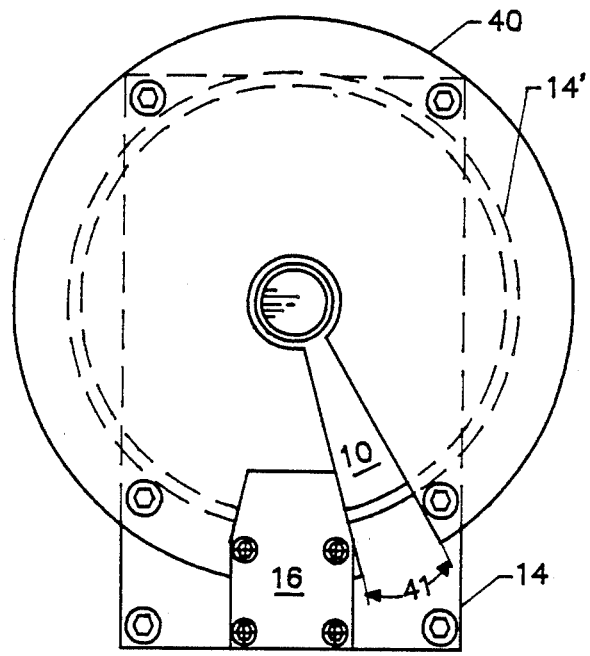
FIG. 6 is a front view of the embodiment of FIG. 4 depicting an optional orientation for the aperture in the mask.

The rotating disk optical transmission monitor of the present invention is intended to be used in connection with sputtering or other processes which deposit thin coatings of a desired material on a substrate. These processes are well known in the art, and it is not deemed necessary to discuss the deposition processes in detail. It is sufficient to note that the rotating disk of the invented monitor should be positioned within the deposition chamber in such a location and at such an attitude that it receives substantially the same accumulation of atoms as does the substrate being processed, or a preselected proportion of that amount. The rate of deposition on the monitoring disk will thus be the same or proportional to the deposition on the substrate being coated.

Referring to FIG. 1, a sectioned view of the monitor disk 10 can be seen attached by thumb screw 13 to hub 11 of shaft 11 of motor 12. The speed of the motor 12 is not critical, but should preferably be fast enough to respond to a change of deposition rate or clarity of the coating being formed within a time acceptable to process control requirements. The reason for this will become evident when the operation of the system is described. The motor 12 is supported by base plate 14 which may have water cooling passages 15 passing therethrough for cooling of the assembly during operation. The motor also can be water cooled, if desired.

The monitor disk 10 is a transparent disk which may be fabricated, for example, from acrylic or polycarbonate sheet material. The thickness is not critical, but it is preferred that the disk be thick enough to be self supporting; a thickness of 0.100 inches has proved to be satisfactory. A clean monitor disk is used for each deposition cycle, and is attached to the motor shaft prior to the start of the deposition process.

The optical system for the monitor is mounted to the base plate 14. The base plate 14 as shown is somewhat narrower than the disk 10 as a matter of convenience, and therefore a shield 14' is provided behind the disk for the purpose of preventing deposition from taking place on the rear surface of the disk. It is desired that all of the deposition take place on one substantially unobstructed surface. Unavoidably, however, a portion of the optical system hardware obstructs a small part of the front surface of disk 10. Typically, about 26° of the area of the disk near its periphery is covered by parts of the optical system and thus, the obstructed area will receive an average coating about 93% as thick as the coating on the unobstructed area. This variance does not result in an error, but is accommodated by calibration of the system.

A light emitting diode and two photocells are used to monitor the transmissivity of the monitor disk, the light being directed through holes drilled in baseplate 14. The light from LED 20 is directed through beam splitter 21 and prism 22 onto photocells 23 and 24. Beam splitter 21 directs a portion (preferably about 50% of the light arriving from LED 20) downward toward photocell 24, and allows the remainder to pass through to prism 22. Prism 22, which is of the total reflecting type, directs all incident light downward to photocell 23. Various lenses 25–29 are shown which focus the light beams on the sensitive areas of the respective photocells. As can be seen, the light falling on photocell 23 has passed through the monitor disk 10 whereas the light on photocell 24 has not.

Figure 3:
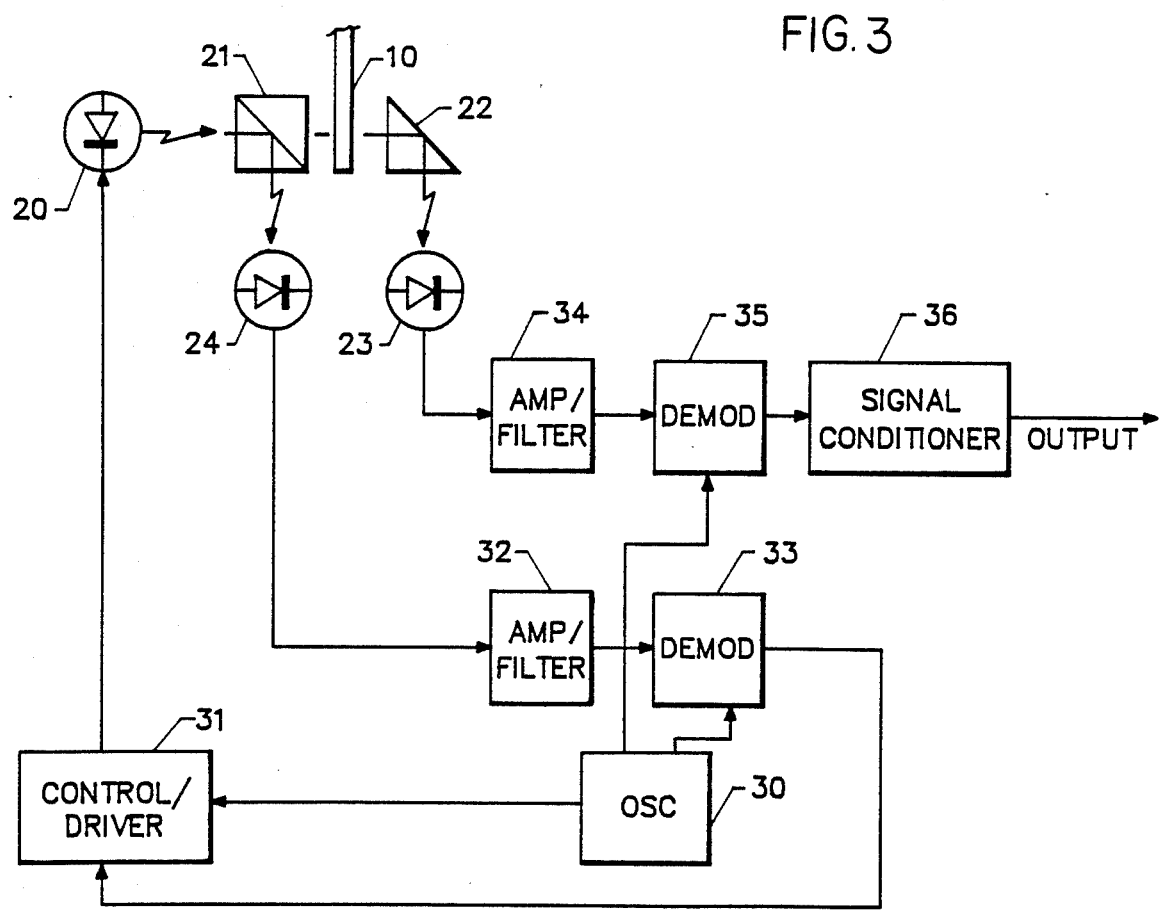
FIG. 3 is a block diagram of the electronic circuitry used in connection with the present invention.

Referring next to the block diagram of FIG. 3, where the optical system just described can be seen shown diagrammatically, LED 20 is shown excited by an AC signal generated by oscillator 30. Control/Driver 31 regulates the amount of power applied to LED 20 in accordance with a feedback signal from photocell 24 (through amplifier/filter 32 and demodulator 33) so as to make the light output of LED 20 constant. The actual drive current to the LED in the presently preferred embodiment of the invention is a unidirectional square waveform with a 50% duty cycle. The light level incident on disk 10 will therefore be constant.

The light reaching photocell 23, however, is attenuated by the optical density of disk 10 so that the signal applied to amplifier/filter 34 and correspondingly the output of demodulator 35 will be a function of the light transmission characteristic of disk 10. If the photocell 23 and its associated circuitry have linear transfer characteristics, the output of demodulator 35 will be proportional to the optical transmissivity of disk 10. Signal conditioner 36 is provided for the purpose of applying any needed calibration factors and/or linearization, if required.

It will be realized that because of the shadowing effect of the prism holder 16, in a dynamic sense, the coating deposited on disk 10 will not be uniform. Very few, if any, atoms from the sputtering cathode will be deposited on the disk in the area covered by prism holder 16 and there will thus be a deficiency of coating in that region. Because of the rotation of the disk, however, all areas of the disk surface receive the same amount of coating deposit as a function of time. Stated in another way, all increments of the disk will receive equal exposure to the arriving atoms due to the continuous rotation of the disk. The portion of the coated area measured by the light beam within prism holder 16 is delayed in time only by the amount of time it takes for an increment of the disk to travel one-half of the shadow angle caused by the prism holder 16. For example, if the disk 10 is rotating at 1.0 revolutions per second (60 rpm) and the total effective shadow angle is 30 degrees, then the measured increment is only $(30/2)/360)(1 \text{ second}) = 0.0417$ seconds (41.7 milliseconds) later than when it had received its last atom of coating material. If this delay time is longer than required for satisfactory process control then a higher motor speed should be used. There is no advantage (or disadvantage) to exceeding the minimum required speed.

The shielding of the disk 10 by prism holder 16 inherently protects the optical system from the deposition process. Not only is there no deposition on the disk in the area of the prism holder, but no deposition on the optics. The optics at the rear of the disk are similarly protected. Consequently, the system may be repeatedly used by merely replacing the disk. There will be no degradation of accuracy of due to obscuration of the optical system.

Assuming that the monitor disk is situated so as to receive the same level of arriving atoms as the substrate being coated, it will be realized that the output of demodulator 35 will be related to the thickness of the film on the substrate being coated, and that the use of suitable calibration factors will allow the monitor to be used to determine the thickness of the deposited film. Because of the shadowing effect of prism holder 16, the portion of the coating on disk 10 which is observed by the optical system will, on the average, be somewhat thinner than the coating on the primary substrate, but as previously noted, this difference can easily be compensated for by an appropriate calibration factor for the system. If the disk is situated in the chamber so as to receive a predetermined ratio of the level of arriving atoms in relation to the substrate being coated, the same calibration rules are applicable. An additional correction factor is simply incorporated to compensate for the increased or decreased coating thickness of the monitor disk as compared to the substrate.

In some cases, however, the optical transmissivity of the coating deposited on the disk may be so low that it is difficult or impossible to make an accurate thickness measurement. This may be the case, for example, if a metallic coating having a thickness of several hundred angstrom units were to be deposited. In such event, the film may be essentially opaque so that no accurate measurement is possible. Using the principles of the present invention, however, an accurate measurement of such a film is possible.

FIGS. 4 and 5 show the apparatus of FIGS. 1 and 2 with a mask 40 installed which allows only a portion of the monitor disk 10 to be exposed at any one time. The angle 41, which defines the open area of the mask, which also will be called the aperture, determines the fractional thickness of the film formed on disk 10 relative to the film deposited on the substrate being processed. For example, if the angle 41 is 18°, the thickness of the coating on disk 10 will be 0.05 or one twentieth of the thickness of the coating on the primary substrate (assuming that the disk is placed so that the deposition on it is at the same rate as is being deposited on the primary substrate).

By suitably selecting a mask which has an appropriate angle 41, the coating on disk 10 can be made to fall within the accurate measuring range of the optical system even though the thickness of the coating on the primary substrate is such that the coating is completely opaque. The thickness of the substrate coating can be determined by multiplying the thickness of the coating on the monitor disk by the inverse of the fraction of 360° represented by angle 41.

For ease of illustration, FIGS. 4 and 5 show the aperture in the mask (angle 41) at a position over the rotating disk 180 degrees from the prism holder 16. It will be realized that this causes a significant time delay from the time when a disk increment is exposed to the coating atoms to when its transmissivity is measured by the light beam at the prism 16 position. If this time delay is a disadvantage to the requirements for process control, the motor speed can be increased or the aperture (angle 41) can be placed as close as possible to the prism holder 16 in the direction of rotation of disk 10. This placement is shown in FIG. 6. When this is done, the time delay from the instant of deposit to the time that the measurement is performed is minimized (assuming clockwise rotation of the disk) and is in fact, then the same as for the unmasked disk operation.

What has been described is a novel optical transmission monitor and film thickness instrument for use in monitoring the deposition of thin films. While presently preferred embodiments of the disclosed instrument have been described so that persons skilled in the art will be enabled to make and use the invention, it is understood that various modifications of the invention will occur to those skilled in the art and such modifications are intended to be covered by the following claims.

We claim:

1. An instrument for determining a characteristic of a film deposited on a substrate during a deoosition process which comprises:
   (a) a supporting structure;
   (b) a monitor substrate in the form of a transparent disk;
   (c) a motor for rotating said disk mounted on said supporting structure;
   (d) shielding means mounted on said supporting structure said means shielding a portion of the surface area of said disk from said deposition process whereby substantially no deposition will occur on the disk within the shielded area:
   (e) a source of light;
   (f) means for directing a beam of said light through said disk within said shielded area; and
   (g) means for generating an electrical signal responsive ot the amount of light passing through said disk.

2. An instrument as recited in claim 1 and further including stabilizing means for stabilizing the intensity of the light incident on said disk.

3. An instrument as recited in claim 1 where said source of light is an LED.

4. An instrument as recited in claim 3 wherein said LED is excited with an AC voltage and wherein said means for generating an electrical signal comprises a photocell and demodulating means for demodulating the output of said photocell.

5. An instrument as recited in claim 1 and further including signal conditioning means to condition said electrical signal whereby the magnitude of said conditioned electrical signal will be a function of the optical transmissivity of said film.

6. An instrument as recited in claim 1 and further including signal conditioning means to condition said electrical signal whereby the magnitude of said conditioned electrical signal will be a function of the thickness of said film.

7. A mehtod for determining a characteristic of a film deposited on a substrate during a deposition process which comprises:
   (a) placing a substrate to be coated in a chamber positioned to be bombarded by particles of the material to be deposited on said substrate;
   (b) placing a transparent disk in said chamber positioned to be bombarded by particles of said material, said positioning being such that the intensity of bombardment on said disk will be a multiple of the intensity of oarticles bombarding said substrate;

(c) shielding a portion of the surface area of said disk from the deposition process whereby substantially no deposition will take place within the shielded area;

(d) rotating said disk whereby different areas of said disk will be shielded from said deposition orocess as said disk rotates;

(e) passing light having a predetermined intensity through said disk within the shielded area; and (f) generating an electrical signal dependent on the amount of said light passing through a portion of said disk.

8. The method as recited in claim 7 where said disk is positioned whereby said multiple is one.

9. The method as recited in claim 7 and further including the step of conditioning said electrical electrical signal will be representative of the optical transmissivity of said film.

10. The method as recited in claim 7 and further including the step of conditioning said electrical signal whereby the magnitude of the conditioned electrical signal will be representative of the thickness of said film.

11. An instrument for determining a characteristic of film deposited on a substrate during a deposition process which comprises:

(a) a supporting structure;

(b) a monitor substrate in the form of a transparent disk;

(c) a motor for rotating said disk mounted on said supporting structure;

(d) a source of light;

(e) an optical system for directing a beam of said light through said disk:

(f) shielding means for preventing deposition on said optical system:

(g) means for generating an electrical signal responsive to the amount of light passing through said disk.

12. An instrument as recited in claim 11 where said shielding means further prevents deposition on a predetermined fraction of the circumference of said said disk;

* * * * *